US007991475B1

United States Patent
Tang et al.

(10) Patent No.: US 7,991,475 B1
(45) Date of Patent: Aug. 2, 2011

(54) HIGH DENSITY MICROMACHINED ELECTRODE ARRAYS USEABLE FOR AUDITORY NERVE IMPLANTS AND RELATED METHODS

(75) Inventors: William C. Tang, Irvine, CA (US); Jian Wu, Irvine, CA (US); Ryan Hainley, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 887 days.

(21) Appl. No.: 11/450,965

(22) Filed: Jun. 8, 2006

Related U.S. Application Data (60) Provisional application No. 60/688,982, filed on Jun. 8, 2005.

(51) Int. Cl.
*A61N 1/05* (2006.01)

(52) U.S. Cl. .............................................. 607/45; 607/2

(58) Field of Classification Search .................. 600/379; 607/55–57
See application file for complete search history.

(56) References Cited

U.S. PATENT DOCUMENTS

| | | | | |
|---|---|---|---|---|
| 5,515,848 | A * | 5/1996 | Corbett et al. | 600/377 |
| 7,212,851 | B2 * | 5/2007 | Donoghue et al. | 600/544 |
| 2004/0006264 | A1 * | 1/2004 | Mojarradi et al. | 600/378 |
| 2008/0195178 | A1 * | 8/2008 | Kuzma | 607/57 |
| 2008/0300652 | A1 * | 12/2008 | Lim et al. | 607/56 |

* cited by examiner

*Primary Examiner* — Carl H Layno
*Assistant Examiner* — Gary A Porter, Jr.
(74) *Attorney, Agent, or Firm* — Robert D. Buyan; Stout, Uxa, Buyan & Mullins (57) ABSTRACT

Devices, systems and methods that comprise or utilize implantable electrode arrays for neural stimulation and/or sensing. In some embodiments, the electrode array is implanted or inserted into the auditory nerve and is used to deliver electrical impulses to/receive data from the auditory nerve in the treatment of hearing disorders.

9 Claims, 6 Drawing Sheets

(a) Glass structure (b) SU-8

(c) SU-8 replica (d) PDMS (e) PDMS embossing tool

Fig. 8

(a) Microfabricated PDMS mold (b) Electrode array sample with SU-08 layer (c) Mold with a embossing pressure and UV exposure (d) Peel off PDMS mold

Fig. 9

HIGH DENSITY MICROMACHINED ELECTRODE ARRAYS USEABLE FOR AUDITORY NERVE IMPLANTS AND RELATED METHODS

RELATED APPLICATION

This patent application claims priority to U.S. Provisional Patent Application No. 60/688,982 filed Jun. 8, 2005, which is expressly incorporated herein by reference.

FIELD OF THE INVENTION

This invention relates generally to the fields of electrical and biomedical engineering and more particularly to implantable electrode arrays useable for neural stimulation and/or sensing.

BACKGROUND

The future development of advanced neuroprosthetic systems is likely to significantly improve the quality of life for persons who suffer from a variety of disorders, including those who are deaf, blind, or paralyzed, etc. Additionally, the development of apparatus and techniques for discretely sensing localized nerve impulses within neural tissue promises to provide new avenues for research and treatment of neurological disorders. However, the development of such advanced neuroprosthetic systems and sensing apparatus will be dependent upon the availability of microelectrode arrays which may be implanted into nerves for the purpose of providing reproducible, localized stimulation or sensing at discrete locations.

One example of an area where advanced neuroprosthetic systems may be of great benefit is in the treatment of hearing disorders. At present, devices known as cochlear implants are being used to restore varying levels of functional hearing in persons who suffer from certain types of hearing loss. The cochlea of the ear is a spiral-shaped, fluid-filled structure that is lined with auditory sensory cells known as "hair cells" which move in response to sound, thereby stimulating the adjacent auditory nerve. The cochlear electrode array resides within a region of the cochlea known as the scala tympani and, thus, is referred to as an "intrascalar electrode." Such intrascalar electrode delivers electrical impulses that bypass the hair cells and stimulate the adjacent portion of the auditory nerve. However, the typical intrascalar electrode is located relatively far from the auditory nerve and is separated from the nerve by the impedance of the modiolar wall. Thus, the spatial resolution of the stimulation currents that each the auditory nerve is relatively low. This lack of spatial resolution limits the number of independent information channels that can be used to transfer auditory information through the auditory nerve to the brain. Moreover, relatively high threshold currents are needed by the intrascalar electrodes, thus resulting in high power consumption which affects the batter life of cochlear implants.

An alternative to the use of intrascalar electrodes is direct stimulation of the auditory nerve by way of an intraneural electrode array that is actually positioned within the auditory nerve. The use of an intraneural electrode array can substantially increase the number of functional channels and by increasing the selectivity and dynamic range of each stimulating electrode. It is believed that, at least in some patients, more accurate tonotopic representations may be obtained if an electrode array is placed directly within the auditory nerve instead of in the scala tympani of the cochlea. Direct stimulation of the auditory nerve may also offer increased spectral resolution and lower power consumption when compared to cochlear implants. The possibility exists to significantly improve human auditory prostheses by Simmon performed the early intranerual electrode implantations, but the relatively large size of the platinum-iridium wire electrodes did neither permit atraumatic insertion, nor accurate placement of these electrodes.

Early attempts in developing intraneural electrodes were based on platinum-iridium wire electrodes, which led to insertion trauma and reduced placement accuracy. In recent years, the development of Microelectromechanical Systems (MEMS) technology (sometimes referred to as Micro Systems Technology or "MST") has made it possible to replace bulky off-chip components with microfabricated counterparts. Using MEMS technology, a number of researchers have fabricated microelectrode arrays intended for implantation in the central and peripheral nervous systems. However, even with the use of MEMS fabrication techniques, certain issues relating to electrode size, the need for electrical wires to communicate and transfer power to the arrays, and the need for hand assembly have remained largely unsolved.

SUMMARY OF THE INVENTION

The present invention provides electrode arrays and intraneural auditory prosthesis having form-fitted implantable micro-electrode arrays and on-chip wireless circuitry. A process known as "flip chip bump bonding" may be used to manufacture these micro-arrays. In a process known as "flip chip bump bonding" a bumped chip is bonded directly to a printed wiring board (PWB). In such process, low-temperature solder is hot-injection-deposited through a mask and onto the PWB.

Devices of the present invention may include various development(s) or improvements over the prior art, including but not necessarily limited to one or more of the following:
 1. Custom-designed circuitry that may be fabricated by standard complementary metal-oxide semiconductor (CMOS) chip manufacturing processes,
 2. Electrodes that may be fabricated with high-precision Deep Reactive-Ion Etching (DRIE),
 3. Flip-chip and solder bump bonding to integrate electronics with the electrodes,
 4. Individual electrodes that may be electrically isolated and held in place with a layer of dielectric at the base and shaped polymer layer around the base,
 5. Etching, deposition, and molding techniques to create the form-fitted contour at the electrode base, and
 6. Data transfer and power delivery to be provided with a wireless, inductive RF system.

Furthermore, this invention creates a three-dimensional, one-chip solution that allows the integration of high density electrodes while avoiding the interconnection problem via wireless, inductive RF telemetry in the CMOS chip.

The present invention provides for (1) accurate and secure placement of the implantable electrodes on the target auditory nerves with a form-fitted geometry, (2) improved reliability, functionality, and manufacturability by eliminating multiple long interconnects between electrodes and signal processing circuits, and (3) greatly enhanced usability and implant duration with wireless telemetry and power delivery to the neural implants.

In accordance with the invention, there are provided electrode arrays fabricated with MEMS for use as implants onto auditory nerve. Such, electrode arrays may be structured with wireless circuitry for both data transmission and power delivery. These electrode arrays may interface with the neurons inside the auditory nerve next to the cochlea and may be used to stimulate those neurons to elicit the sensation of sound, thereby restoring some amount of hearing to deaf patients who have total damage to the cochlea. The electrode arrays of the present invention may also act as neural recorders for research purposes, recording the electrical impulses generated from healthy cochlea in response to sounds.

The invention is intended for implanting onto human auditory nerves to restore hearing functions for profoundly deaf patients and to record electrical signals generated from sound in healthy subjects. The wireless telemetry and the electrode array design in this invention can also be applied to other neural prostheses including retinal and vestibular implants, as well as to serve as a general-purpose miniaturized device for chronically stimulating and recording the nervous system in electrophysiological and behavioral experiments involving conscious animals.

A flip chip assembly bonds the electrode array and the vendor fabricated electronic chip. The term "flip-chip" refers to the electronic component that is mounted directly onto another silicon substrate in a 'face-down' manner. Electrical connection is achieved through conductive bumps built on the surface of the chips, which is why the mounting process is 'face-down' in nature. During mounting, the chip is flipped on the substrate, with the bumps being precisely positioned on their target locations. Because flip chips do not require wire bonding, their size is much smaller than their conventional counterparts. Physically, the bump on a flip-chip is exactly just that—a bump formed on a bond pad of the die. Bumps serve various functions: 1) to provide an electrical connection between the die and the substrate; 2) to provide thermal conduction from the chip to the substrate, thereby helping dissipate heat from the flip chip; 3) to act as spacer for preventing electrical shorts between the die circuit and the substrate MEMS device; and 4) to provide mechanical support to the flip-chip.

In at least some embodiments of the invention, electrode arrays of the present invention may be fabricated by initially bump bonding silicon wafer to CMOS chip. Columns approximately 750 mm in height are created by bulk micromachining this silicon wafer with deep reactive ion etching (DRIE). At this height the final electrodes can penetrate to the center of the auditory nerve, thereby stimulating and recording from the maximum number of neurons. In some embodiments, columns of varying height may be formed, such that the resultant electrodes will vary in length and will thereby stimulate nerve fibers at varying depth (or in various planes) within the acoustic nerve. Since the number of stimulated neurons correlates to the fidelity of the implant, the intraneural electrode arrays of the present invention may elicit better sound sensation than current cochlear implants. Also, DRIE etching uses a photo-definable masking layer that enables a substantially higher density of electrodes than the use of dicing saws. As a result, the present invention is able to achieve more than 100 electrodes in a 1.5 square millimeter area. Each electrode may have a diameter of about 80 microns and the space between two adjacent electrodes may be about 50 microns. The columns may be sharpened into a needle shape with a two-step isotropic etching, reactive ion etching (RIE) and HNA wet etching process. The passive array may be activated by deposition of iridium to form the electrode tips and conformal coating with a layer of biocompatible Parylene C. The tips may be exposed in the final step by selectively removing Parylene C from the tip area. The surface roughness on the electrodes can be reduced by refinement of the tip-shaping process. Also, the Parylene C coating may contribute to further reduction or elimination of surface roughness.

Further in accordance with the present invention, a CMOS chip may be flip-chip bump bonded to a silicon wafer before the electrode array fabrication. The CMOS chip will have both wireless communication and DSP functions for neural recording and stimulation. This on-chip circuitry will eliminate the need for an interconnection between the electronic chip and the MEMS electrode. The most significant advantages of using wireless link and on-chip DSP instead of transcutaneous electrical wires include ease of implant surgery, vastly improved mechanical robustness, and enabling chronic implantation with minimal complications.

Further aspects, elements and details of the present invention are described in and may be understood from the following detailed description and the accompanying drawings.

BRIEF DESCRIPTION OF THE DRAWINGS

FIGS. 3A'-3E' are diagrams showing steps in a method for fabricating an alternative embodiment of the implantable device of FIG. 2 wherein the electrodes are of varied length.

DETAILED DESCRIPTION

The following detailed description, the drawings and the above-set-forth Brief Description of the Drawings are intended to describe some, but not necessarily all, examples or embodiments of the invention. The contents of this detailed description, the accompanying drawings and the above-set-forth brief descriptions of the drawings do not limit the scope of the invention or the scope of the following claims, in any way.

Figure 1:
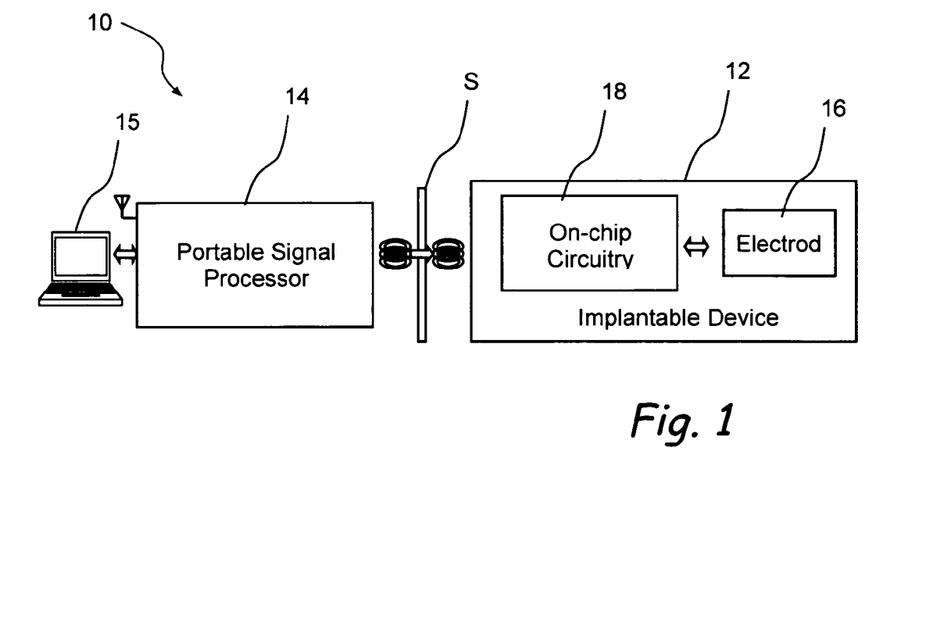
FIG. 1 is a schematic diagram of an auditory neural prosthesis system of the present invention.

FIG. 1 is a schematic diagram of a auditory neural prosthesis system 10 comprising an implantable device 12 and a signal processor 14. The implantable device comprises an intraneural electrode array 16 with integrated on-chip circuitry 18 which can communicate in wireless fashion through the skin S with the signal processor 14. The electrode array 16 with on-chip circuitry 18 is implanted such that the electrodes of the array 16 are inserted into the auditory nerve of a human or animal subject. A bi-directional RF telemetry link is used to transfer both data and power from the signal processor 14 to the implantable device 12. The signal processor 14 may be battery powered and may be carried by the subject, subcutaneously implanted on the subject or otherwise maintained in sufficient proximity to the on chip circuitry 18 to allow data and power to be transmitted via the telemetry link. The processor 14 may deal with the data by using certain algorithms. The processor 14 may also be connected to a computer work station 15 by a Bluetooth or Wi-Fi link to advance data processing.

Figure 2:
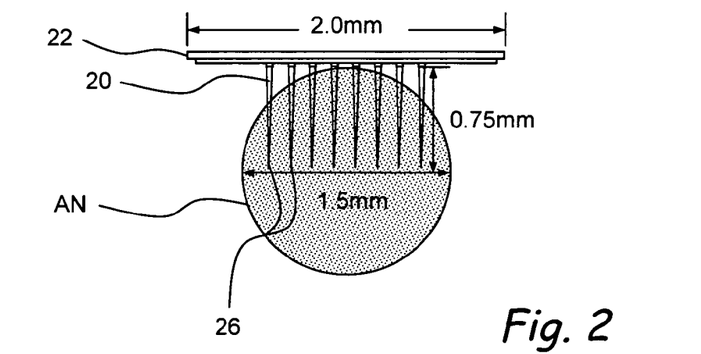
FIG. 2 is a side-view schematic diagram of one embodiment of an implantable device of the present invention having an array of intraneurally insertable electrodes attached to a chip having on-chip circuitry.

FIG. 2 shows one embodiment 12a of the implantable device 12. In this embodiment 12a, the electrode array 16a comprises a plurality of elongate electrodes 20 having sharpened distal ends 22. The electrodes 20 are operatively inserted into the auditory nerve AN, as shown, while the on-chip circuitry 18a resides in juxtaposition to the auditory nerve AN. It has been reported that the auditory nerve AN in an adult human typically ranges in diameter from 1.06 to 1.5 mm. In this embodiment, the each electrode 20 is approximately 750 µm in length. This, when the electrodes 20 are advanced to their maximum extent into the auditory nerve AN, the distal tips 22 of the electrodes 20 will have traveled approximately half way through the nerve fiber, as shown in the diagram of FIG. 2.

In a process for manufacturing the implantable device 12, as more fully described herebelow, customized circuitry is first fabricated on a chip by standard CMOS technique. The electrode array 16 is etched into or otherwise formed on the bottom of a silicon wafer. The circuitry-bearing chip is flip-chip bonded to the top of the silicon wafer and interconnections are made by solder between the two layers. Each individual electrode 20 is isolated by underfilling. This design proposes a 3D one-chip solution, which avoids the interconnection problem between the circuitry and the microelectrode array, and shows more potential for achieving higher density of electrode. The inductive RF telemetry transmits both data and power to the implantable device through tissue.

Manufacture of the Electrode Array

Figure 3:
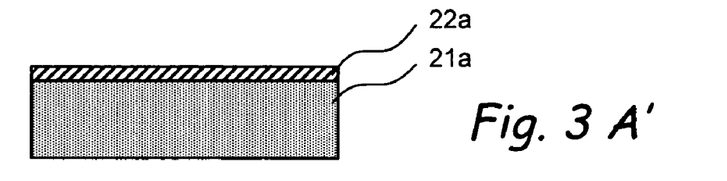
FIGS. 3A-3E are diagrams showing steps in a method for fabricating the implantable device of FIG. 2.
Figure 3A:
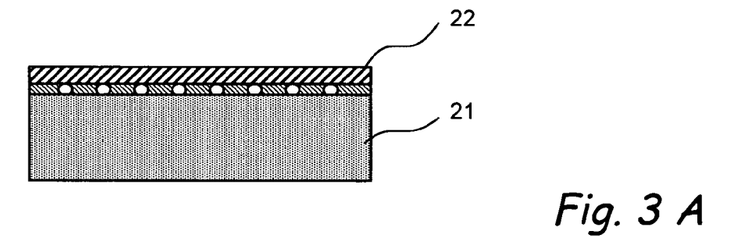
Figure 3B:
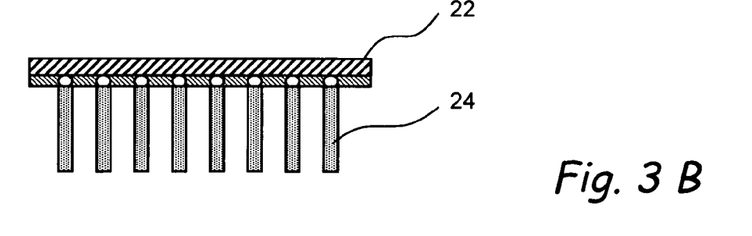
Figure 3C:
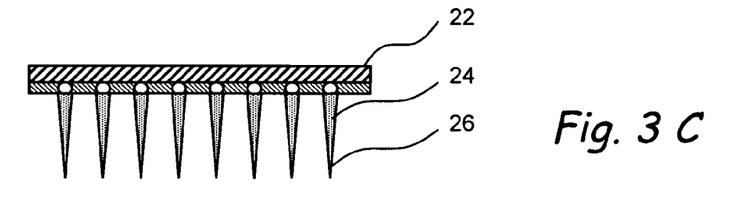
Figure 3D:
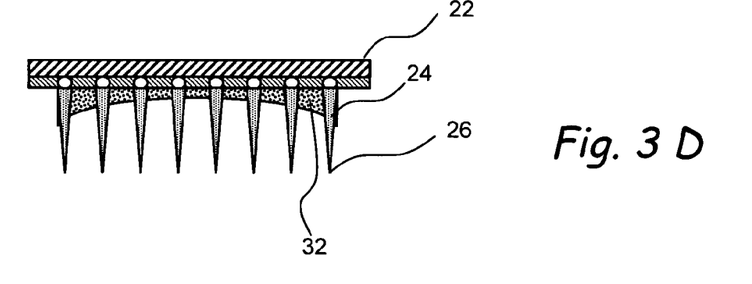
Figure 3E:
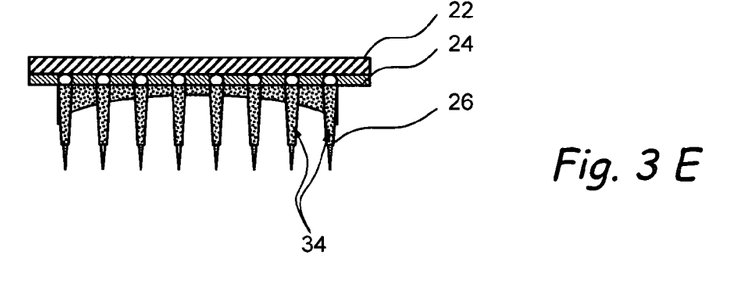
Figure 4:
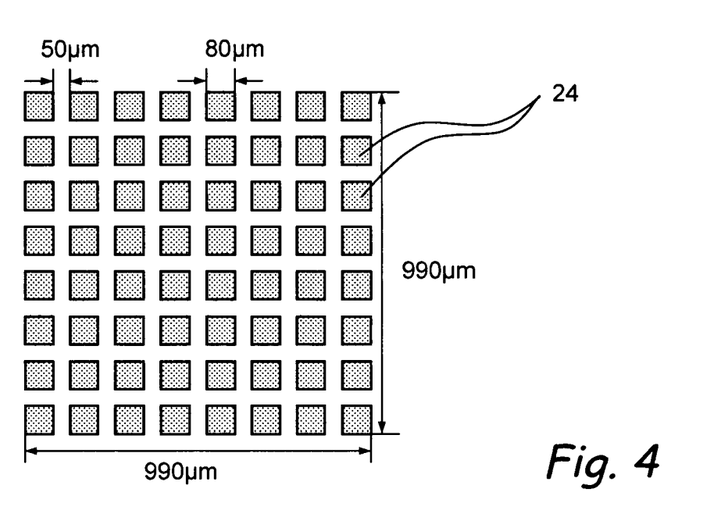
FIG. 4 is a bottom-view schematic diagram of the workpiece shown in FIG. 3A.
Figure 8:
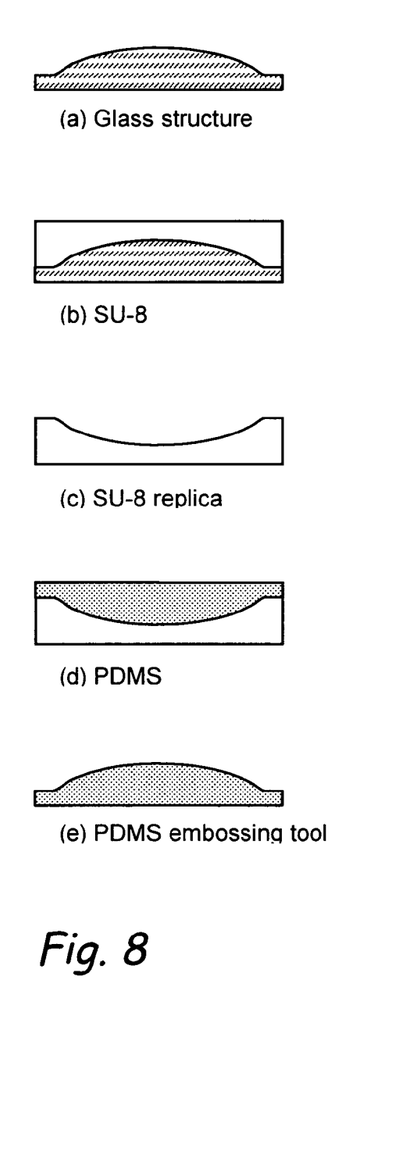
FIG. 8 is a schematic diagram showing the use of an embossing tool in fabrication of a device of the present invention.
Figure 9:
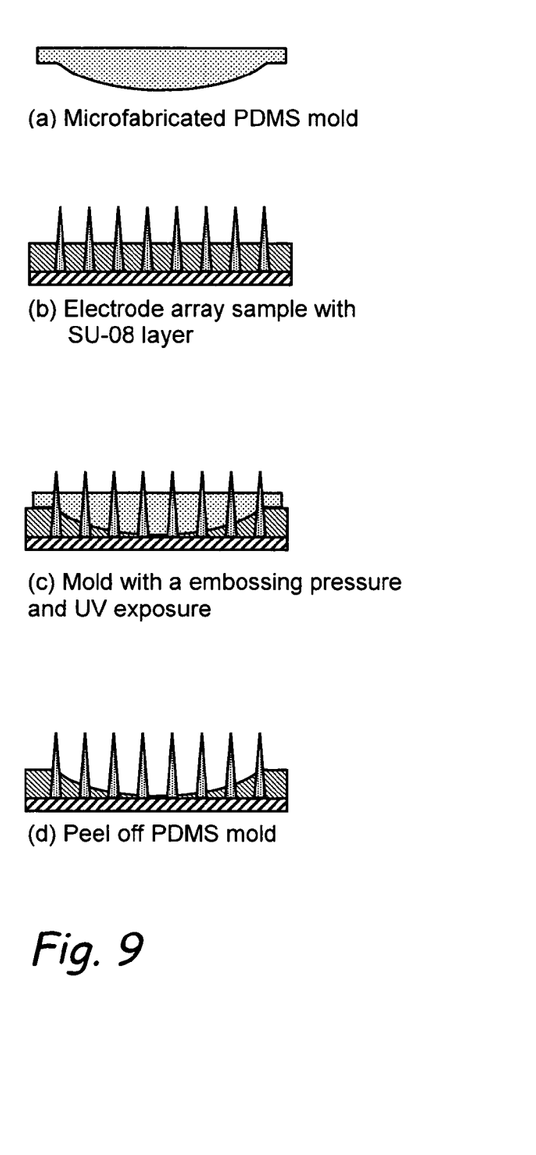
FIG. 9 is a schematic flow diagram showing steps in a process for blow molding a device of the present invention.

FIGS. 3A-3E show a process for forming the electrode array 16a of the implantable device 12a shown in FIG. 2 using CMOS technology. This process begins, a shown in FIG. 3A, with a highly doped silicon wafer 21 having A CMOS chip 22 bonded thereon. Next, as shown in FIG. 3B, a Bosch Deep Reactive Ion Etch (DRIE) is used to remove or cut away portions of the wafer 20 so as to form a number of substantially square silicon columns 24 on the underside of the wafer. In the example shown in the drawings, these columns 24 form an 8 electrode×8 electrode array that is less than 1 mm² in area, as shown in FIG. 4. Each column 24 is then wet etched by dipping in HNA acid to form a sharp needle tip 26 on each column 24 as shown in FIG. 3C. Subsequently, the sharp needle tips 26 are coated with Iridium for charge transfer. As seen in FIG. 3D, a photoresist material 30, such as SU-8 (a near-UV photoresist used for MEMS fabrication), is then filled into the gaps among the columns 24 and molded with a PDMS mold (see FIGS. 8 and 9) to form a concave curved surface 32 thereon. This curved surface 32 is generally of a shape that mates with the convex outer surface of the auditory nerve AN. In this manner, the curved surface 32 will make substantially abutting contact with the outer surface of the auditory nerve AN, thus providing additional stability and also limiting the extent to which the electrodes 20 may be advanced into the auditory nerve AN. As shown in FIG. 3E, polyimide coating is then applied to each column 24 and a portion of such coating is then removed from a distal portion of each column 24, thereby exposing the sharpened distal tips 26 and forming an array of individual electrodes 20a.

It is to be appreciated that, in the example of FIGS. 3A-3E, the electrodes 20a are of equal length. Thus, as shown in FIG. 2, when fully advanced into the auditory nerve AN, those electrodes 20a at the center of the array will advance to the center of the auditory nerve fiber while those electrodes 20a on the periphery of the array will remain in the periphery of the auditory nerve fiber. Also, the conductive distal portions of all of the electrodes 20a will thus be disposed in a horizontal plane within the auditory nerve AN and will connect only with nerve fiber(s) that run through that particular horizontal plane. The nerve fibers above and below this horizontal plane will not receive direct impulses from the electrodes 20a. Also, many of these equal length electrodes 20a may redundantly deliver impulses directly to only certain fiber(s) that pass through the horizontal plane and not to other nerve fibers that pass through other portions of the auditory nerve AN.

To deliver impulses directly to more auditory nerve fibers and to minimize unnecessary redundancy in stimulation of the auditory nerve fiber(s), it may be desirable in some embodiments of the invention to vary the length of the individual electrodes 20a. FIGS. 3A'-3E' show an example of an alternative manufacturing process for forming an implantable device 12a having an electrode 16a with electrodes 20a of varying length. In this example, a 10×10 electrode array is created in a 1 mm² area by way of a bulk-machining process.

As seen in FIG. 3A' this process begins with silicon wafer 21a bump bonded to a signal-processing and wireless-communication CMOS chip 22a. The bump bonding process is known in the art and is described in more detail herebelow. A 10×10 array of individual columns 24a is then created in the silicon wafer 21a by micromachining this silicon wafer 21a with DRIE. The widths (i.e., diameters) of the columns 24a range from 70 µm in the center of the array to 80 µm at the edges of the array, increasing by increments of 2 µm per column. Each column 24a is then sharpened into a needle shape with an isotropic etchant solution of 20% Hydrofluoric, 70% Nitric, and 10% Acetic acid (HNA). Various concentrations of acid in this etchant solution can result in different column geometry. This etching process also shortens the columns 24a to different lengths due to the differences in column width (i.e., the wider columns have greater mass and therefore remain longer while the narrower columns have less mass and therefore become shorter). In this example, after completion of the etchant step, the columns 24a vary in length from 200 µm to 750 µm. A lift-off iridium coating is then applied to the columns 24a. The columns 24a are then coated with a layer of biocompatible Parylene C and such Parylene C coating is then removed from the distal portions of the columns 24a by $O_2$ plasma, thereby forming the individual electrodes 20b. As seen in FIG. 3E', when these electrodes 20b are inserted into the auditory nerve AN, the exposed tips of the electrodes 20b will reside within a number of different horizontal planes within the nerve AN, thereby delivering impulses to nerve fibers located in those various horizontal planes.

On-Chip Circuitry

Figure 5:
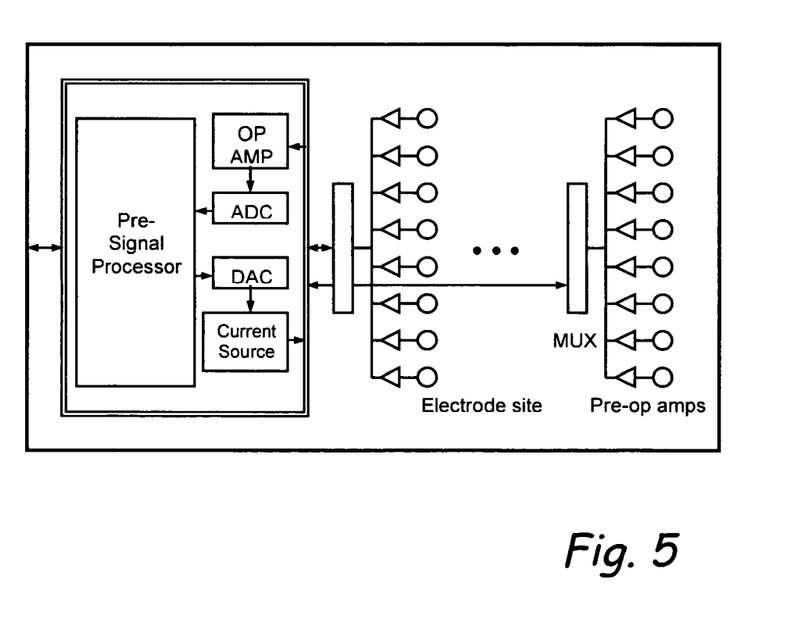
FIG. 5 is a block/flow diagram of one embodiment of on chip circuitry useable in this invention.

In this example, the on-chip circuitry is fabricated by AMIS ABN 1.5 µm process. FIG. 5 shows a block/flow diagram of one embodiment of the on chip circuitry 18 useable in this invention. This circuitry contains both neural recording and stimulation function.

To record the neural signals, Pre-amplifiers are first to use to amplify the neural signals, which usually are much weak. Time division multiplexers then are employed for each eight electrodes to save more external leads and discriminate signals from different record sites. Before the signals are sent to the signal processor, they are amplified and digitalized. The processor codes the signals into a train for advanced exploration. On the other hand, to stimulate the auditory nerve AN, the signal sequence is first decoded, and converted to analogy signals, which will trigger the current source to generate bi-phase current pulses to fire the nerve fibers.

In the 64-channel neural signal recording circuit shown in the example of FIG. 5, low-noise pre-amplifiers are necessary for the active microelectrodes because of the relatively weak signal. Time division multiplexers are employed for each group of eight electrodes to conserve external leads and discriminate signals from different recording sites. Before further processing, the signals are amplified with a second-stage operational amplifier, and then digitized with an 8-bit A/D converter. The chip 22 or 22*a* is fabricated with AMI 0.5 μm triple-metal and double-poly CMOS technology with a die size 1.5×1.5 mm². Low-noise amplifier is employed in our design. The 8:1 multiplexer is implemented by full CMOS switches. The 8-bit charge redistribution successive approximation A/D converter is chosen in this design to take advantage of the minimal amount of analog hardware in order to meet our primary design goal of low-power consumption and small layout area. The successive converters apply a binary search algorithm to determine the closest digital word to match an input signal. The ADC sampling rate is 100 kS/sec in order to sample from 8 channels. The maximum magnitudes of Integral Nonlinearity (INL) and Differential Nonlinearity (DNL) are less then 0.8 LSB. The total power consumption of the chip is lees than 100 μW.

Wafer Bonding

Figure 6:
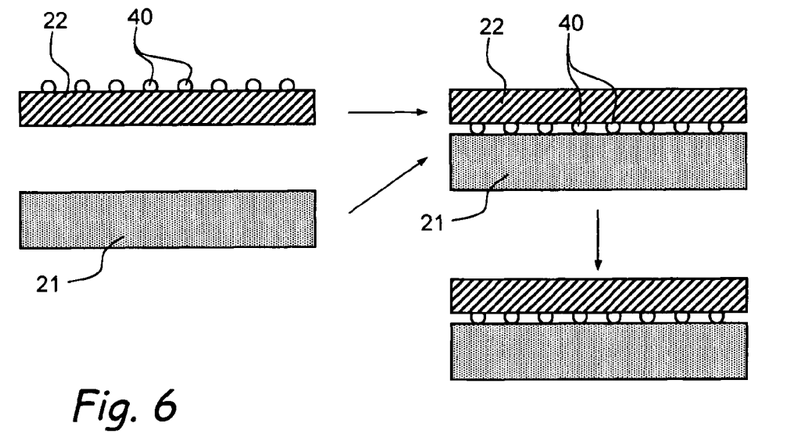
FIG. 6 is a schematic diagram of steps in a process for flip chip bonding of a circuit bearing chip to a silicon wafer substrate in accordance with the present invention.

In this example, the fabricated electronic chip 22 is bonded to the silicone wafer 21 by a "flip chip" process whereby the circuit bearing chip 22 is mounted on the silicone wafer 21 in a 'face-down' manner. FIG. 6 shows a schematic diagram of the process flow for flip chip bonding. In accordance with the art of flip chip bonding, electrical connection is achieved through conductive bumps 40 that are built into the circuit formed on the surface of chip 22, which is why the mounting process is 'face-down' in nature. During mounting, the chip 22 is flipped onto the wafer 21, with the bumps 40 being precisely positioned on their target locations to correspond to the position of each individual electrode 24. Because no wire bonding is required, the chip 22 may be smaller in size than a conventional chip having the same functional circuitry. Physically, each bump 40 on the flip-chip is exactly just that—a bump formed on a bond pad of the die. Bumps 40 serve various functions: 1) to provide an electrical connection between the die and the substrate; 2) to provide thermal conduction from the chip to the substrate, thereby helping dissipate heat from the flip chip; 3) to act as spacer for preventing electrical shorts between the die circuit and the substrate MEMS device; and 4) to provide mechanical support to the flip-chip.

The open spaces 42 between the flip chip surface and the substrate are filled with a non-conductive adhesive 'underfill' material. Various types of underfill adhesives may be used. One example of a suitable underfill adhesive that may be used for this purpose is a two part cold cured epoxy resin adhesive available as DELO-DUOPOX™ available from Delo Industrial Adhesives, Landsberg, Germany. Such underfill material may serve to protect the bumps 40 and the circuitry of the chip 22 from moisture, contaminants, and other environmental hazards. Also, this underfill material mechanically locks the flip chip 22 to the silicone wafer 21, thereby reducing the differences between the expansion of the flip chip 22 and the wafer 21. This prevents the bumps 40 from being damaged by shear stresses caused by differences between the thermal expansions of the chip and the wafer substrate 21. Meanwhile, it provides the isolation at the root of the electrode.

Inductive RF Telemetry

Figure 7:
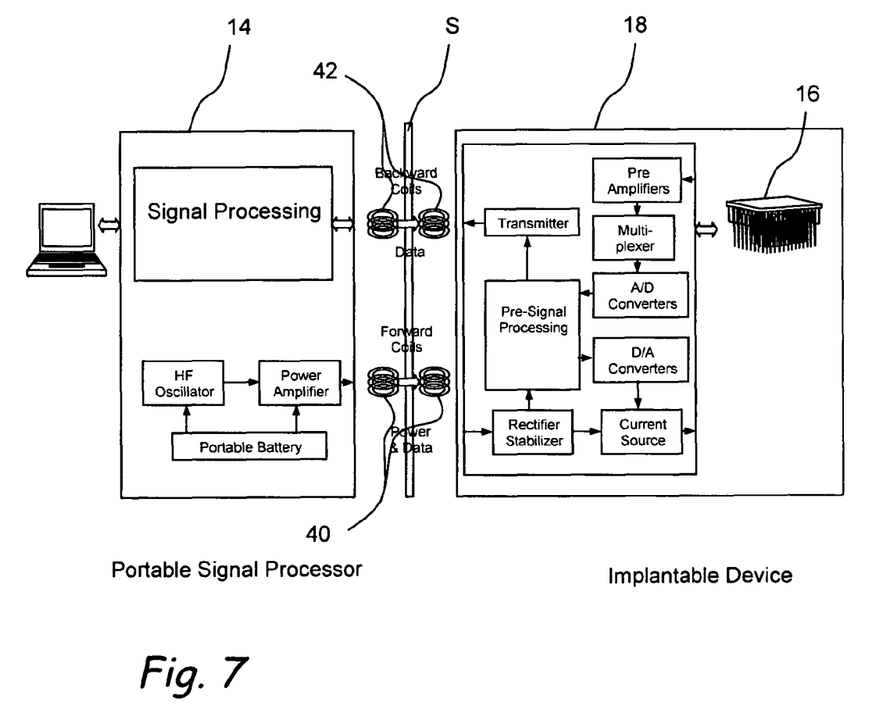
FIG. 7 is a more detailed block/flow diagram of an auditory neural prosthesis system of the present invention.

As illustrated in the flow diagram of FIG. 7, in wireless embodiments of the present invention, inductive radio frequency (RF) telemetry may be used to provide communication between the signal processor 14 and the on chip circuitry 18 of the implantable device 12 or 12*a*. Such wireless connection avoids the risk of infection associated with the use of wires to penetrate through biological tissue. Data and power signals can be transmitted by means of two inductively coupled coils 40, 42 on the both sides of the tissue (e.g., through the skin and adjacent tissues surrounding the ear). The forward coil 40 is driven by a class E power amplifier, which can achieve high transfer efficiency, to transmit power and data to the implantable device. A voltage regulator on the on chip circuit 18 stabilizes the received power and supplies other components on the chip 22 or 22*a*. Stimulation data through the forward coil 40 are converted to bi-phase pulse trains, then sent to the electrode array 16 or 16*a* to fire the target nerve fibers. A transmitter included in the on chip circuitry 18 collects the pre-processed recording data, and sends such data outside the tissue by a backward coil 42. The manufacturer and/or implanting professional may tune the transcutaneous link to optimize transmission and/or to account for variations in implant size and shape of the coils, location of the implant, misalignment and displacement tolerance, power and regulation requirements, efficiency, communication bandwidth, and power supply.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise stated or unless doing so would render the embodiment or example unsuitable for its intended use. Also, where the steps of a method or process are stated in a particular order, the order of such steps may be changed or varied unless otherwise stated or unless doing so would render that method or process unsuitable for its intended use. All reasonable additions, deletions, modifications and alterations are to be considered equivalents of the described examples and embodiments and are to be included within the scope of the following claims.

What is claimed is:

1. A system for treating a hearing disorder in a human or animal subject, said system comprising:
   (a) an electrode assembly comprising i) a chip; ii) a silicon wafer bonded to the chip; iii) electrodes of varying length extending from the chip, said electrodes comprising columns of silicon of varying length formed on and extending from one side of the silicon wafer, each column having a sharp distal tip, an electrically conductive iridium layer on each of said columns of silicon and an insulating Parylene C layer on top of the electrically conductive iridium layer, the insulating Parylene C layer being absent from a distal portion of each column thereby exposing the electrically conductive iridium layer on a distal portion of each electrode, said electrodes of varying length being insertable into an auditory nerve of the subject such that the electrodes of varying length penetrate to varying depths within the auditory nerve; and iv) circuitry on the chip in communication with the exposed iridium layer on the distal portion of each electrode, said circuitry being configured to perform both neural recording and stimulation functions; and (b) a signal processor is communicably coupled with the circuitry on the chip, said signal processor configured to perform neural recording and to deliver stimulation through the electrodes to nerve fibers at varying depths within the auditory nerve.

2. A system according to claim 1 wherein the signal processor is sufficiently portable to be carried by the subject.

3. A system according to claim 1 further comprising wireless telemetric apparatus whereby the signal processor communicates with the on chip circuitry.

4. A system according to claim 3 wherein the wireless telemetric apparatus transmits both power and data.

5. A system according to claim 3 wherein the wireless telemetric apparatus comprises a forward coil and a rearward coil.

6. A system according to claim 1 wherein the plurality of electrodes comprises more than 100 electrodes in a 1.5 square millimeter area.

7. A system according to claim 6 having a curved surface that is configured to substantially abut the outer surface of the auditory nerve when the electrodes are inserted to varying depths within the auditory nerve.

8. A system according to claim 1 wherein spacing between adjacent electrodes is from about 40 to about 60 microns.

9. A method for improving the hearing of a human or animal subject using a system according to claim 1, said method comprising the steps of:
  implanting the electrode assembly such that the electrodes extend to varying depths within an auditory nerve of the subject; and
  using the signal processor to perform neural recording and to deliver stimulation through the electrodes to nerve fibers at varying depths within the auditory nerve.

* * * * *